(12) United States Patent
Ahluwalia et al.

(10) Patent No.: US 7,790,444 B2
(45) Date of Patent: Sep. 7, 2010

(54) BIOREACTOR FOR STUDYING THE EFFECTS OF IMPOSED STIMULI ON CELLULAR ACTIVITY

(75) Inventors: Arti Ahluwalia, Fosdinovo (IT); Federico Vozzi, Eboli (IT); Giovanni Vozzi, Eboli (IT); Nicola Forgione, Pisa (IT); Antonino Previti, Pisa (IT); Valerio Rossi, Nodica (IT); Cristiano Scarpa, Sassari (IT)

(73) Assignee: Universita' Degli Studi di Pisa, Pisa (IT)

( * ) Notice: Subject to any disclaimer, the term of this patent is extended or adjusted under 35 U.S.C. 154(b) by 688 days.

(21) Appl. No.: 11/629,917

(22) PCT Filed: Jun. 16, 2005

(86) PCT No.: PCT/IB2005/001691

§ 371 (c)(1),
(2), (4) Date: Jan. 11, 2007

(87) PCT Pub. No.: WO2005/123258

PCT Pub. Date: Dec. 29, 2005

(65) Prior Publication Data

US 2008/0274539 A1 Nov. 6, 2008

(30) Foreign Application Priority Data

Jun. 18, 2004 (IT) .............................. PI2004A0046

(51) Int. Cl.
 C12M 1/00 (2006.01)
 C12M 3/00 (2006.01)
(52) U.S. Cl. ............... 435/294.1; 435/288.1; 435/305.2

(58) Field of Classification Search ............. 435/294.1, 435/305.2, 41, 176, 288.1; 422/146; 210/601
See application file for complete search history.

(56) References Cited

U.S. PATENT DOCUMENTS 4,889,812 A * 12/1989 Guinn et al. ............. 435/286.7

(Continued)

FOREIGN PATENT DOCUMENTS

EP 276154 7/1988

(Continued)

*Primary Examiner*—William H Beisner
*Assistant Examiner*—Michael Hobbs
(74) *Attorney, Agent, or Firm*—Dennison, Schultz & MacDonald (57) ABSTRACT

A bioreactor device for studying the effects of physical, chemical, mechanical and electromagnetic stimuli on the cellular activity. In particular, the device uses a sensorized premixing chamber (1), a culture chamber (2) for observing the development of the cells by a microscope (40). Output signals are transmitted to a control unit for amplifying and filtering the signals (50), which transmits the treated signals to a computer (52). To another control unit (51) actuating electrovalves (20), (21) and (22) are connected that adjust the introduction of gas in the premixing chamber. The culture medium is drawn from the premixing chamber (1) through a duct (4) and its flow is adjusted by a peristaltic pump (30). The culture medium crosses then the culture chamber (2) and continues its path in a duct (3), returning again in the premixing chamber (1). At the outlet of the culture chamber (2) the duct has a sample point (23) for picking up an amount of culture medium to analyze. Immediately before, along the duct, a temperature sensor is provided (24) that transmits a signal to the control unit (50) by an electrical cable (9).

16 Claims, 5 Drawing Sheets

U.S. PATENT DOCUMENTS

| | | | |
|---|---|---|---|
| 4,918,019 A * | 4/1990 | Guinn | 435/286.5 |
| 4,937,196 A | 6/1990 | Wrasidlo et al. | |
| 5,257,128 A * | 10/1993 | Diller et al. | 359/395 |
| 5,563,068 A * | 10/1996 | Zhang et al. | 435/295.2 |
| 5,612,188 A * | 3/1997 | Shuler et al. | 435/29 |
| 5,795,710 A * | 8/1998 | Park | 435/1.1 |
| 2004/0058407 A1 * | 3/2004 | Miller et al. | 435/29 |
| 2006/0019385 A1 * | 1/2006 | Smith et al. | 435/348 |
| 2006/0051733 A1 | 3/2006 | Lowe | |
| 2006/0258000 A1 * | 11/2006 | Allen et al. | 435/325 |

FOREIGN PATENT DOCUMENTS

| | | |
|---|---|---|
| WO | 86/02378 | 4/1986 |

* cited by examiner

BIOREACTOR FOR STUDYING THE EFFECTS OF IMPOSED STIMULI ON CELLULAR ACTIVITY

FIELD OF THE INVENTION

The present invention relates to a bioreactor for studying the effects of stimuli of physical, chemical, mechanical and electromagnetic nature on cellular activity, for applications in many fields among which: in tissue engineering for development of biological constructs; in the industrial field for pharmacological "testing", and in the cosmetic field for studying allergologic reactions to the developed products.

DESCRIPTION OF THE PRIOR ART

It is well known that each biological tissue during its evolution and its normal activity is subject to physical and chemical stimuli that both determine its pathological and physiological status and affect its normal function. For this purpose, systems capable of reproducing physical or chemical stimuli have been sought in order to study its influence on the normal cellular activity.

Presently, real systems are known that reproduce a pressure stimulus, for studying the influence on the gangliar or endothelial cells. Other known systems reproduce a laminar flow, or turbulent flow, for simulating the permeation of nutrients through cellular membrane, as normally occurs in any biological tissue owing to blood flow.

Concerning isobar cell culture two systems are known:
a first system studies the links between the increase of the pressure and apoptosis in gangliar cells. It consists of a special culture chamber that is brought to high pressures and is monitored by a mercury sphigmomanometer. The atmosphere in the chamber consists of a 5% mixture of $CO_2$ and the temperature is kept fixedly at 37° C.;
another system studies the links between the pressure variation and the release of endotheline 1. It consists of a cell culture plate with 24 chambers, coated by adhesive tape with which the upper edge of the plate is sealed, and at each chamber a hole is made where the predetermined pressure is applied and monitored by a pressure valve connected to a sphigmomanometer.

So called flow bioreactors also exist, which provide a chamber for cell culture that is arranged in series with a nutrient flow system. The applications of such bioreactors are various, such as the study of pathologies, the regeneration of cardio-muscular tissues, the development of hepatic functional substitutes, the regeneration and the testing of cartilage.

Flow bioreactors have been studied for high density cultures. In fact, the flow of nutrients that passes through a bioreactor allows a much easier perfusion of the same and a most effective removal of the cellular catabolites. These systems increase the growth speed of cellular mono-layers up to a confluence from 100% up to 200% and optimize the function, the morphology and the differentiation of the cells.

On the market, the many bioreactors differ from one another essentially for a variety of types of the culture chambers:

"Rocking Culture System", consisting of a fixed base with an oscillating plate and a culture bag in which a gaseous mixture flows through special connectors on the upper part of the bag. The conveyance of the mass and of the gas, as well as the mixture of the culture medium, are achieved through the oscillation of the plate. The effects of the waves generated on the surface and of turbulence cause a considerable increase of the coefficient of volumetric transfer of nutrients with respect to a static culture.

"Spinner Bioreactor System" having flasks with rotatable blades that cause the perfusion of oxygen and the distribution of the nutrients. For controlling the pH and the temperature it is necessary to put the system in an incubator.

"Spinner-Air Lifted Bioreactor" that adopts a system for immobilizing the cells consisting of porous disks connected to each other by a stiff part made of steel.

"Rotary Cell Culture System" also called rotating wall, having a rotating cylindrical chamber that contains a co-rotating cylindrical membrane, for exchanging the gas and for oxygenation.

"Airlift Bioreactor", consisting of an elongated chamber arranged up to a vertical position, in whose lower part the mixture of gas is put in. The gas inserted from below causes the reduction of the density of the liquid contained in the tube. This causes a circulation of the culture medium through the inner tube towards the outermost zone of the tube.

"Hollow-Fiber Bioreactor", having a network of artificial semipermeable capillaries that, once soaked by the culture medium for diffusive phenomena, it supplies oxygen to the cells, taking nutrients and removing the catabolites from the cellular metabolic paths as well as cleaning other inhibitors of the cell growth.

"Flat Bed Perfusion System", comprising a flat chamber containing co-cultures of stroma, i.e. a mesh of connectival fibres normally of reticular nature. The cell is perfused by the culture medium.

"Stirred Tank". This device has an electric motor that wheels some blades having a variable geometry and arrangement. They are very similar to the "Spinners" and they allow cultures with "microcarriers" or cultures in suspension. The blades are kept still by a steel part during a decantation step or during the intervention of an operator, to avoid to damage the cells or the "microcarriers".

"Micro-Cell Culture Analog", consisting of a micro culture chamber made by standard lithography and "etching" techniques and has micro-chambers that are arranged in series with different cellular cultures in order to analyse the effect of a same drug on different cells for studying its pharmacokinetiks.

The main limit of most of these systems is that they are not autonomous, since they require an incubator in order ensure required values of pH and temperature in the chamber. The presence of the incubator does not allow, in particular, the use of a computer for following in real time the progressive change of the parameters in order to adjust them during the experiment.

Bioreactors also exist where the presence of an incubator is not necessary; however, the structure of the chamber for cell culture does do not allow to follow the experiment in real time, by means of optical and/or fluorescence microscope, and then to determine the development of the cellular processes.

In conclusion, autonomous bioreactors do not presently exist that are at the same time capable of keeping the pressure the pH and the temperature in a culture chamber and to change it quickly in a controlled manner, as well as capable of generating in the cells a fixed flow of culture medium, with possibility of looking in real time at what is happening inside.

SUMMARY OF THE INVENTION

It is an object of the present invention to provide a device with the functions of a bioreactor that uses culture chambers that are easily modellable and conformable, and that allow the use of transducers and regulators, for monitoring in real time what happens in a culture chamber and for adjusting the parameters and the physical-chemical stimuli that are simulating physiological and/or pathological conditions.

Another object of the invention is to provide a device with the function of bioreactor where a flow of culture medium is present that allows a reduction of the amount of culture medium used for each experiment that is from 10 to 30 times less with respect to other devices present on the market, with considerable savings concerning both the amount of culture medium and the analysis of the substances in it contained.

A further feature of the present invention is to provide a bioreactor having means for conveying the culture medium in the culture chambers that do not damage the cells and cellular aggregates, do not have means for stirring, gas bubbling or other mechanical moving parts in the culture chamber.

These and other objects are achieved by a bioreactor for monitoring cellular activity in the presence of physical, chemical and mechanical stimuli, whose characteristic is of providing:

at least one culture chamber having an inlet and an outlet;
   a premixing chamber, separated from said at least one culture chamber, to prepare a culture medium;
   a circuit connected to said inlet and said outlet and comprising said premixing chamber;
   means for conveying in a controlled manner said culture medium through said circuit;
   means for generating at least one physical-chemical stimulus that has to be applied to the cells being tested, said stimulus being selected from the group of: temperature, pH, pressure or combination thereof;
   means for controlling said means for generating at least one physical-chemical stimulus, so that said or each stimulus reaches predetermined values.

Advantageously, said means for controlling comprise a specially developed software, which by a graphic interface easy to operate by each user allows both setting the parameters of the experiment and looking in real time at what happens to the cells.

This way an analysis in real time is allowed of a culture chamber without having the need to use an incubator surrounding the culture chamber.

In particular, said culture chamber is made of silicone rubber and is shaped in such a way that a desired laminar flow of the culture medium is created that can be outlined by a computer aided design program.

Preferably said cell is made of at least two parts that can overlap, where at least one has a recess in such a way that once overlapped to the other a passage for the culture medium is provided.

Advantageously, along said passage for the culture medium at least one of said parts that can overlap provides a glass slide for laboratories, in order to allow a microscope observation of the implanted cells. Said two parts that can overlap can be pressed on each other by two stiff plates kept together by releasable coupling means.

Preferably, said means for conveying in a controlled manner said culture medium through said culture chamber comprises:

an inlet and outlet duct communicating with said culture chamber, to form a closed circuit with a separated premixing chamber;
   a peristaltic pump installed along said duct;
   an introduction point for drugs or other substances that boost or inhibit cellular activity arranged upstream from the culture chamber;
   a sample point downstream of the culture chamber for taking samples to analyse;
   a temperature sensor arranged upstream from the cell.

In particular, said premixing chamber comprises:

a container of inert material;
   a plug of inert material;
   means for operatively measuring the physiological parameters of the culture medium.

Preferably, said container of inert material is shaped as a glass flask.

Advantageously the means for operatively measuring the physiological parameters of the culture medium can comprise:

a pH sensor immersed in the culture medium present in said premixing chamber;
   a pressure sensor for measuring pressure in said premixing chamber;
   sensors for measuring chemical species such as $O_2$, $CO_2$, NO, etc.

Advantageously, in and at the bottom of the premixing chamber, a conical frustum concave structure is present where said pH sensor is arranged, in order to preserve it from a direct contact with possible bubbles of gas, which is introduced in said premixing chamber for adjusting the flow of culture medium and keeping it at a predetermined pH.

Preferably, means are provided for operatively adjusting the physiological parameters of the culture medium comprising:

inlet/outlet ducts for a gas, for example air and $CO_2$, into/away from said premixing chamber for changing its pH and the pressure;
   a flow of thermostated fluid in a duct that surrounds said premixing chamber, for changing its temperature.

Preferably, the means for monitoring and controlling the physical-chemical stimuli applied to the cells in the culture chamber are selected from the group comprised of:

an optical sensor for detecting bubbles in the cell culture chamber;
   a sensor for detecting deformation and mechanical stresses.

Advantageously, several culture chambers can be connected by means of ducts of predetermined length for simulating the behaviour of biological organs even complex, so that the cells contained in the chambers that are arranged upstream produce metabolites that, transported by the culture medium, feed the cells contained in the chambers that are arranged downstream.

Advantageously more chambers connected to each other are integrated on a single miniaturized support, in particular of stiff material, creating a circuit for the flow of culture medium that feeds, in a predetermined way and in succession, all the culture chambers.

Advantageously, said support of stiff material is made through a process of microforming, in particular, by photolithography and/or electroerosion.

Advantageously said support blocks the cells and the ducts with at least one glass slide of transparent material, allowing the microscope observation of the development of the cells contained in the chambers.

Advantageously, said inlet and outlet ducts of gas into/away from said premixing chamber can be operated by electrovalves driven by an electrical control unit.

Preferably, the bioreactor uses an electronic control unit for amplifying and filtering the electrical signals coming from the sensors, for measuring said physiological parameters of the culture medium, and located separately from said electrical drive control unit for the electrovalves, to avoid electromagnetic interferences.

BRIEF DESCRIPTION OF THE DRAWINGS

The invention will now shown with the following description of an exemplary embodiment thereof, exemplifying but not limitative, with reference to the attached drawings wherein:

FIG. 4 shows a cross sectional view of the culture chamber;

DESCRIPTION OF THE PREFERRED EMBODIMENTS

Figure 1:
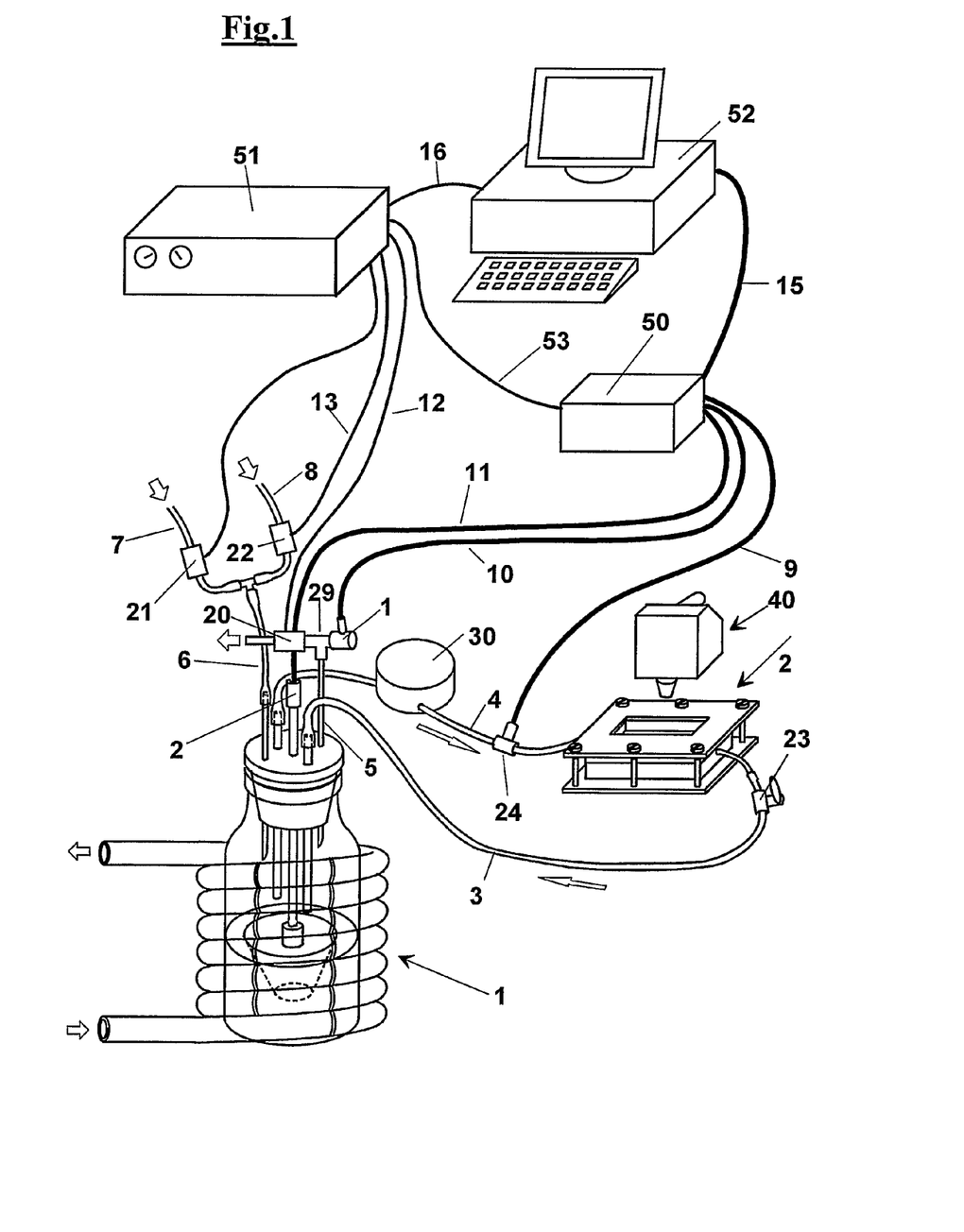
FIG. 1 shows the bioreactor with the devices to it connected for measuring and adjusting from the outside all the biological and physical parameters of interest.

In FIG. 1 an aggregate view is shown of a bioreactor for studying the effects of physical, chemical, mechanical and electromagnetic stimuli on cells activity.

In particular, the device uses a sensorized premixing chamber 1 that has the task of preparing a culture medium that is used for feeding the cells, which are arranged in a culture chamber 2, for eventually observing the development of the cells by a microscope 40. The signals at the outlet of the sensors are transmitted to a signal amplifying and filtering control unit 50, which transmits the treated signals to a computer 52 that saves them by an I/O data acquisition board.

Said computer is connected to a control unit 51 that operates electrovalves 20, 21 and 22, which adjust the introduction of air and carbon dioxide in the premixing chamber. Said control unit 51 is connected to control unit 50 by an electrical cable 53, in order to eliminate the interference of the electric supply network with the signal amplification and filtering system.

The culture medium is drawn from the premixing chamber 1 by duct 4 and its flow is adjusted by a peristaltic pump 30. The culture medium crosses then culture chamber 2 and continues its path through duct 3, returning again in the premixing chamber 1. At the outlet of culture chamber 2 the duct has a pick up point 23 for spilling out a sample of culture medium to analyse. Immediately before, along the duct, a temperature sensor is provided 24 that transmits a signal to the control unit 50 by electrical cable 9.

Premixing chamber 1 comprises a pH sensor 2, which transmits a signal to the control unit 50 by electrical cable 10. Anther parameter determined in the premixing chamber is pressure, through a pressure sensor 1 that transmits a signal to the control unit 50 by electrical cable 10.

The premixing chamber contains a controlled environment by a controlled introduction of air through duct 7 and of $CO_2$ through duct 8, which flow then in a duct 6. Such introductions are controlled respectively by electrovalves 21 and 22, operated by control unit 51. Premixing chamber 1 has also a gas outlet duct 5, which is also controlled by a servomechanism 20 operated by the same control unit 51, which allows keeping the pressure fixed in the bioreactor as imposed by the software.

The control of the physical-chemical and physiological parameters is carried out in order to follow the data imposed by the software through an algorithm of PID type, so that the system is steady, and this would not have happened if an ON/OFF control had been used, and corrections are made only when the system alone cannot turn back to the starting equilibrium, in order to reduce the effects coming from the outer environment and to simulate as far as possible an homeostasis of the cellular system.

Figure 2:
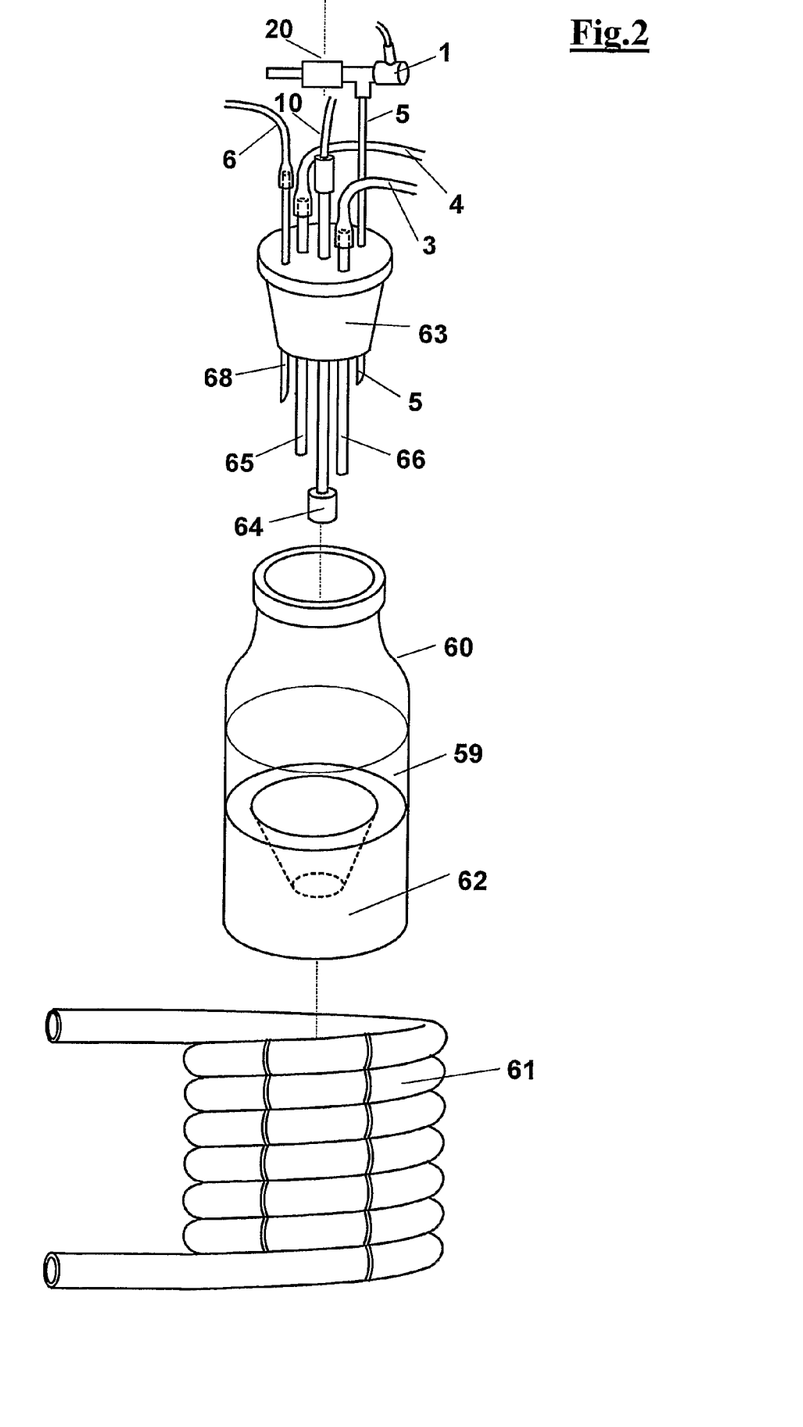
FIG. 2 shows an exploded view of the premixing chamber for the culture medium.

The premixing chamber is described in more detail in FIG. 2. In particular, it comprises a glass container 60 or a container of other inert material, shaped for example as a flask, closed hermetically with a silicone plug 63 that allows to house the sensors and to arrange a plurality of inlet/outlet stiff ducts, to which flexible ducts are connected. In particular, the plug 63 is crossed: by a duct 68 for introducing gas (air or $CO_2$), which is connected to flexible duct 6; by duct 5, which has at one end a T-shaped sleeve to support pressure sensor 1 and at the other servomechanism 20 for the exit of the gas; by the inlet duct 65 and outlet duct 66, which are connected respectively to the flexible ducts 4 and 3 for the culture medium. Furthermore, plug 63 allows the movement of a stem for the pH sensor 64, which is connected to electrical cable 10.

On the bottom of container 60, a base 62 is made of silicone rubber that has a frustum conical recess for reducing the space about pH sensor 64, to obtain a more accurate measure, avoiding that the added gas changes the pH.

The temperature of the culture medium 59 present in the container 60, is adjusted by a flow of liquid at a chosen temperature flowing in a duct 61 surrounding the container 60.

FIGS. 3 to 6 show some examples of the embodiment of a culture chamber.

Figure 3:
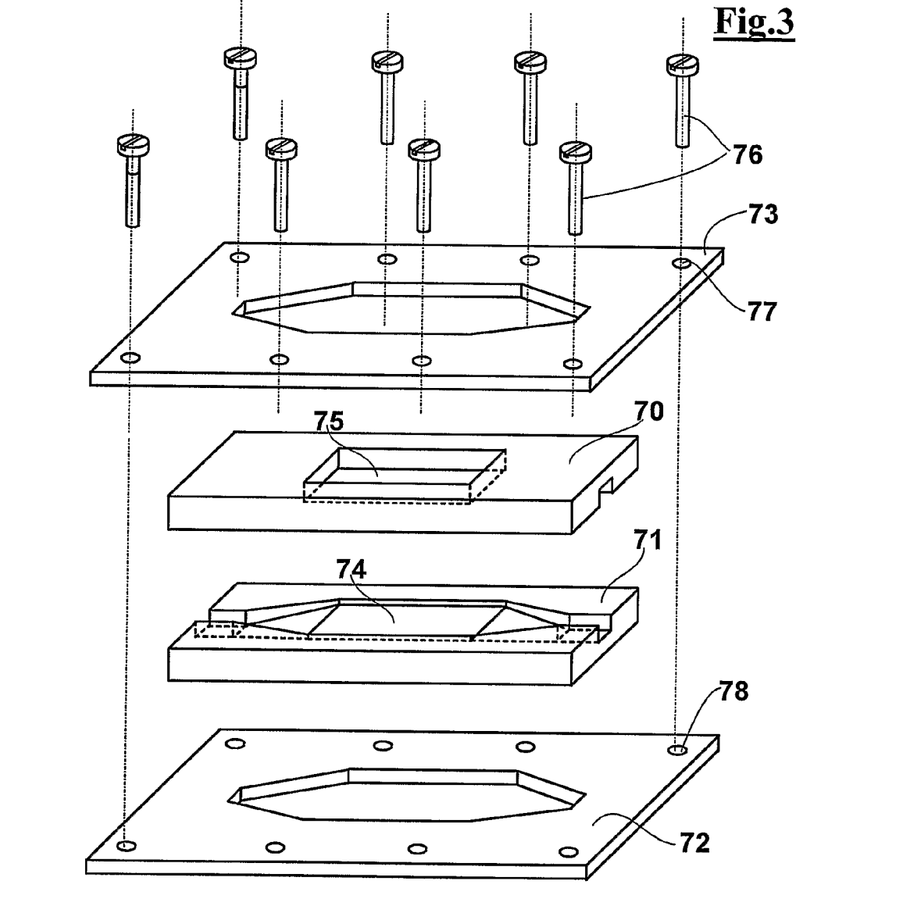
FIGS. 3 and 4 show respectively an exploded perspective view and a cross sectional view of an exemplary embodiment of culture chamber.
Figure 4:
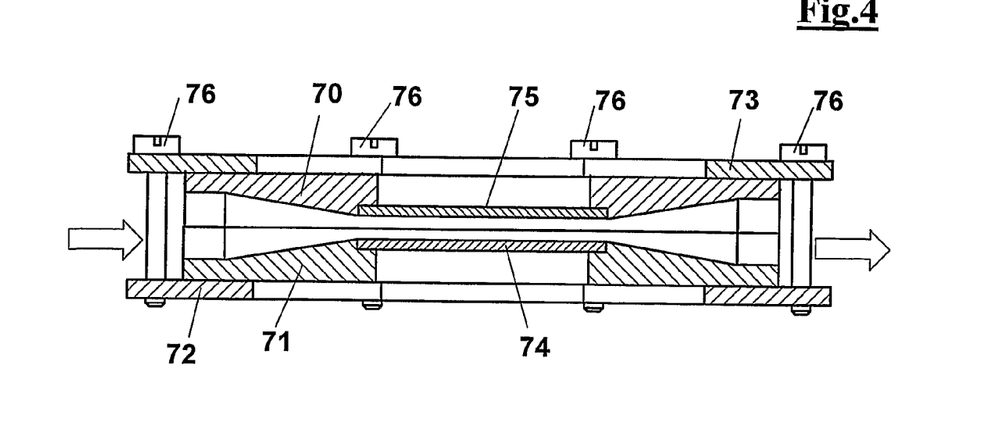

In particular, in FIGS. 3 and 4 an exploded view and a cross sectional view are shown respectively of a particular type of cell where the shape of the duct is studied to ensure a laminar flow of culture medium. The cell comprises two parts of silicone material, a lower part 71 and an upper part 70 symmetric to each other. They comprise respective glass slides 74 and 75 that allow the observation by a microscope of the development of the cells previously deposited on the glass slides same. The two parts of silicone rubber are kept together by two stiff plates 72 and 73, for example of metal, kept together by screws 76.

Figure 5:
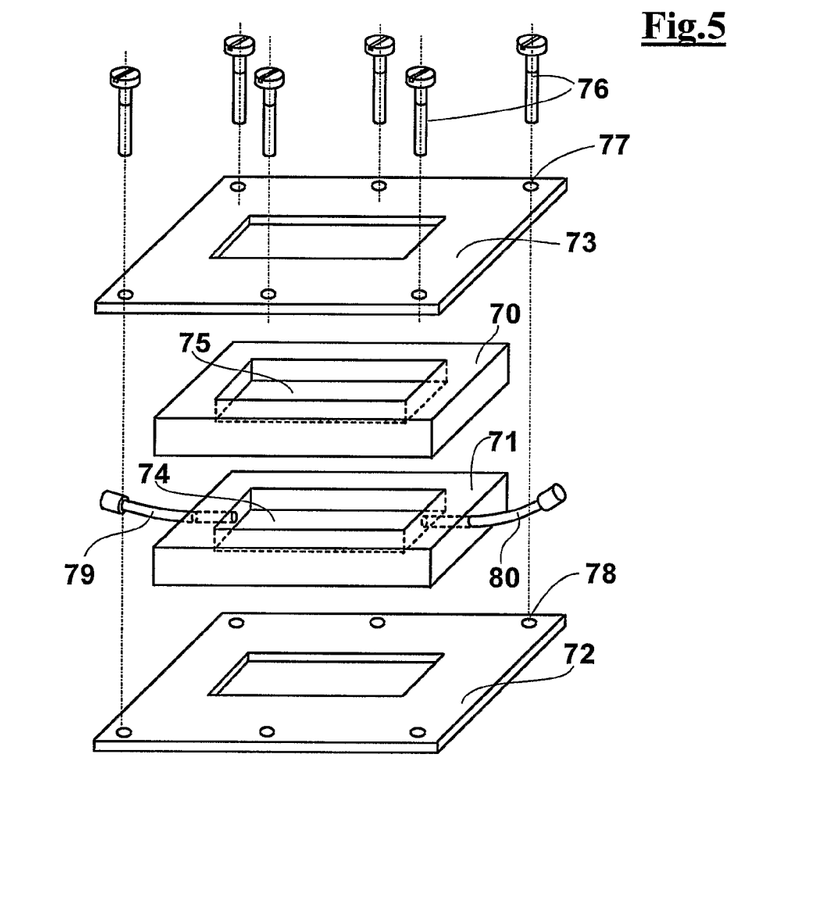
FIGS. 5 and 6 show respectively an exploded view of the assembling arrangement and a cross section of another exemplary embodiment of culture chamber.
Figure 6:
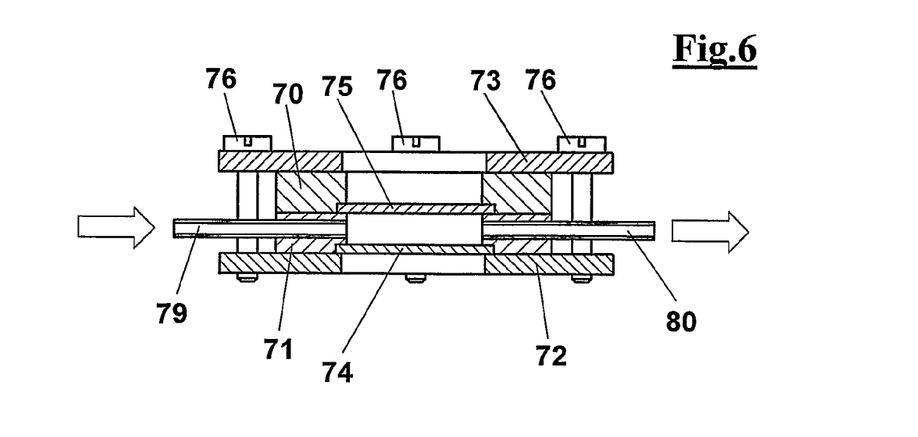

FIGS. 5 and 6 show respectively an exploded view and a cross section of another exemplary embodiment of culture chamber, in which the flow of the culture medium is allowed by ducts 79 and 80. Even in the present example the cell comprises two parts of silicone rubber 70 and 71, comprising respective glass slides 74 and 75 for allowing the observation of the cells. The two parts of silicone rubber are then kept together by stiff plates 73 and 72 connected by screws 76.

Figure 7:
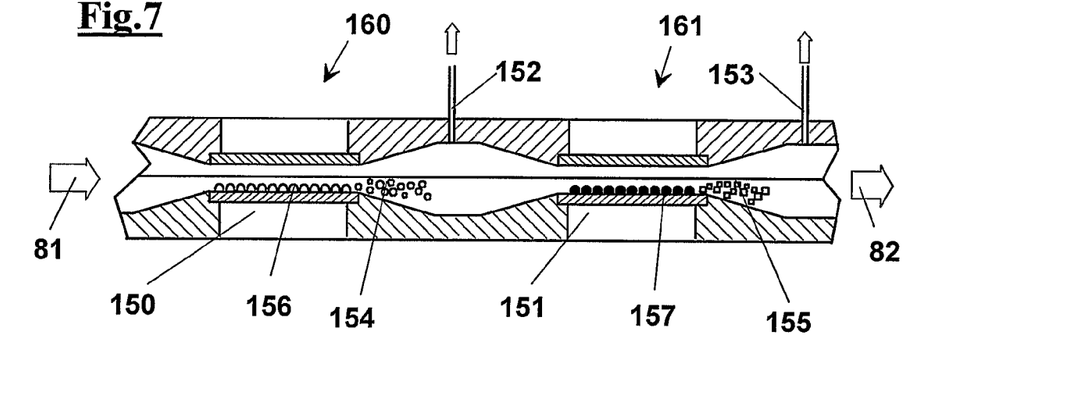
FIG. 7 shows a succession of two culture chambers in series.

As shown in FIG. 7, several culture chambers can be connected together in series or in parallel so that the products of the cells cultivated in the chambers arranged upstream feed the cells in the chambers arranged downstream, in order to simulate physiological systems, such as the respiratory system, the cardiovascular system, the metabolic system, the feeding system, etc. In the example treated chamber 160 and chamber 161 are located in series upstream and downstream with respect to the flow 149 of culture medium; on glass slide 150 are deposited for example "cells a" 156, which make "metabolites a" 154 and on glass slide 151 are deposited for example "cells b" 157 that make "metabolites b" 155 feed themselves with "metabolites a" 154.

Downstream from each cell a pick up point 152 and 153 can be provided for spilling out an amount of culture to analyse.

Figure 8:
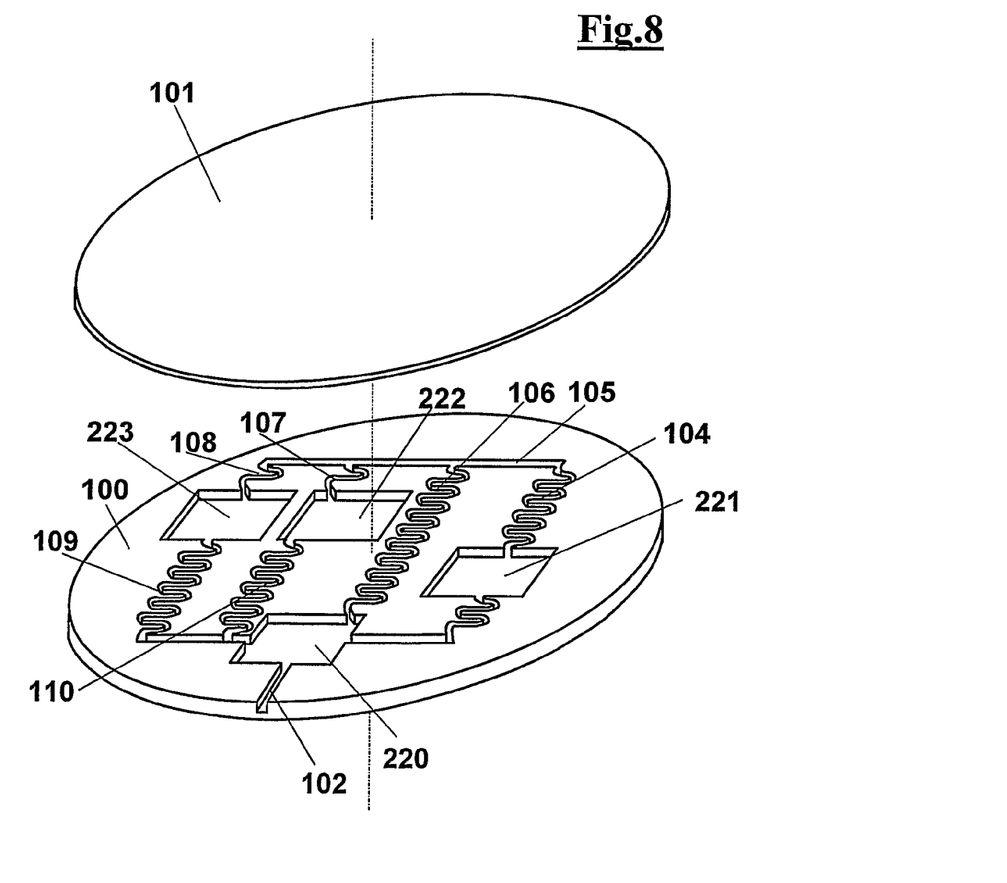
FIG. 8 shows an application of a assembly of culture chambers connected in series and in parallel that simulate the operation of a biological apparatus.

In FIG. 8 an example is described of combination of several culture chambers connected in series and in parallel by means of more or less long ducts (102, 103, 104, 105, 106, 107, 108, 109, 110) and integrated on a single support 100, executed by lithography on the body of the support same. The channels thus obtained in the support can be closed above with a glass slide 101 that covers the whole support 100, or alternatively with more glasses that close the single chambers. In particular, are used four chambers that contain respectively: human or murine hepatic cells 220, endothelial cells 222, adipocytes 223, pancreatic cells 221, which completely simulate the metabolism of an organism. The biological processes of the cells is monitored individually by measuring the metabolites and the proteins in standard conditions, in sampling carried out near each chamber. The substances that can be detected are various, such as albumin, cholesterol, glucose, potassium, lactate, sodium, proteins total, triglycerides, urea and other.

In the example described a culture medium inlet channel is used 102 to feed the hepatic cells in chamber 220, from which, through ducts 109 and 110 the culture medium reaches respectively the adipocytes in chamber 223 and the cells endothelial in chamber 222, connected in parallel. From these chambers cells, through the ducts 107, 108 and 105, the culture medium reaches hepatic cells in chamber 220 through duct 106 and through duct 104 running through the pancreatic cells in chamber 221.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. A bioreactor for monitoring cellular activity in the presence of physical, chemical and mechanical stimuli, said bioreactor comprising:
   at least one culture chamber having an inlet and an outlet;
   a premixing chamber, separated from said at least one culture chamber, to prepare a culture medium;
   a pH sensor immersed in the culture medium present in said premixing chamber;
   a circuit connected to said inlet and said outlet and comprising said premixing chamber;
   means for conveying in a controlled manner said culture medium through said circuit;
   means for generating at least one physical-chemical stimulus that has to be applied to the cells being tested, said stimulus being selected from the group of temperature, pH, pressure or combination thereof; and
   means for controlling said means for generating at least one physical-chemical stimulus, so that said or each stimulus reaches predetermined values;
   wherein a frustum conical concave structure is present in and at the bottom of the premixing chamber, where said pH sensor is arranged, in order to protect said pH sensor from direct contact with bubbles of gas.

2. A bioreactor for monitoring cellular activity, according to claim 1, wherein said culture chamber is made of silicone rubber and is shaped in such a way that through said culture chamber a laminar flow of the culture medium is achieved.

3. A bioreactor for monitoring cellular activity, according to claim 1, wherein said culture chamber is made of at least two parts that can overlap, where at least one part has a recess in such a way that once overlapped to the other part a passage for the culture medium is provided.

4. A bioreactor for monitoring cellular activity, according to claim 3, wherein, along said passage for the culture medium at least one of said parts that can overlap comprises a glass slide for laboratories arranged to operatively allow a microscope observation of cells implanted on it.

5. A bioreactor for monitoring cellular activity, according to claim 4, wherein said two parts that can overlap can be pressed on each other by two stiff plates kept together by releasable coupling means.

6. A bioreactor for monitoring cellular activity, according to claim 1, wherein said means for conveying in a controlled manner said culture medium through said culture chamber comprises:
   an inlet and an outlet duct communicating with said culture chamber, to form a closed circuit with a separated premixing chamber;
   a peristaltic pump installed along said duct;
   an introduction point for drugs or other substances that boost or inhibit cellular activity arranged upstream from the culture chamber;
   a sample point downstream of the culture chamber for taking samples to analyze;
   a temperature sensor arranged upstream from the cell.

7. A bioreactor for monitoring cellular activity, according to claim 1, wherein said premixing chamber comprises:
   a container of inert material;
   a plug of inert material;
   means for operatively measuring the physiological parameters of the culture medium.

8. A bioreactor for monitoring cellular activity, according to claim 7, where the means for operatively measuring the physiological parameters of the culture medium comprise:
   a pH sensor immersed in the culture medium present in said premixing chamber;
   a pressure sensor for measuring pressure in said premixing chamber;
   sensors for measuring chemical species, selected from the group consisting of $O_2$, $CO_2$, and NO.

9. A bioreactor for monitoring cellular activity, according to claim 7, wherein means are provided for operatively adjusting the physiological parameters of the culture medium comprising:
   inlet/outlet ducts for a gas, such as in particular air and $CO_2$, flowing into/away from said premixing chamber for changing its pH and the pressure;
   a flow of thermostated fluid in a duct that surrounds said premixing chamber, for changing its temperature.

10. A bioreactor for monitoring cellular activity, according to claim 1, wherein several culture chambers are connected by means of ducts of predetermined length for simulating the behavior of biological organs even complex, so that the cells contained in the chambers arranged upstream produce metabolites that, transported by the culture medium, feed the cells contained in the chambers that are arranged downstream.

11. A bioreactor for monitoring cellular activity, according to claim 10, wherein more chambers connected to each other are integrated on a single miniaturized support, in particular of stiff material, creating a circuit for the flow of culture medium that feeds, in a predetermined way and in succession, all the culture chambers.

12. A bioreactor for monitoring cellular activity, according to claim 11, wherein said support blocks the cells and the ducts with at least one glass slide of transparent material, allowing the microscope observation of the development of the cells contained in the chambers.

13. A bioreactor for monitoring cellular activity, according to claim 9, wherein said inlet and outlet ducts of gas flowing into/away from said premixing chamber, are associated to electrovalves driven by an electrical control unit.

14. A bioreactor for monitoring cellular activity, according to claim 1, wherein said means for monitoring and controlling the at least one physical-chemical stimulus is an optical sensor for detecting gas bubbles in the cell culture chamber.

15. A bioreactor for monitoring cellular activity, according to claim 1, wherein said means for monitoring and controlling the at least one physical-chemical stimulus is a sensor for detecting deformation and mechanical stresses.

16. A bioreactor for monitoring cellular activity, according to claim 1, wherein said premixing chamber comprises a means for monitoring and controlling the at least one physical-chemical stimulus, said means being selected from the group consisting of:
- an optical sensor for detecting gas bubbles in the cell culture chamber; and
- a sensor for detecting deformation and mechanical stresses.

* * * * *